United States Patent [19]

Russell

[11] Patent Number: 5,504,089
[45] Date of Patent: Apr. 2, 1996

[54] 2-HYDROXYALKYL-BENZIMIDAZOLES, -QUINAZOLINES AND -BENZOTHIAZOLES AS POTASSIUM CHANNEL AGONISTS

[75] Inventor: Keith Russell, Newark, Del.

[73] Assignee: Zeneca Limited, London, England

[21] Appl. No.: 242,521

[22] Filed: May 13, 1994

[30] Foreign Application Priority Data

May 17, 1993 [GB] United Kingdom .................. 9310069

[51] Int. Cl.$^6$ .................. A61K 31/54; A61K 31/535; C07D 239/86; C07D 235/12
[52] U.S. Cl. .................. 514/259; 514/267; 514/362; 514/364; 514/368; 514/397; 514/399; 544/251; 544/284; 544/287; 548/126; 548/178; 548/179; 548/306.1; 548/310.1
[58] Field of Search .................. 548/126, 178, 548/179, 306.1, 310.1; 544/251, 284, 287; 514/259, 267, 362, 364, 368, 397, 399

[56] References Cited

U.S. PATENT DOCUMENTS

| | | | |
|---|---|---|---|
| 3,666,769 | 5/1972 | Jones et al. | 548/178 |
| 5,258,390 | 11/1993 | Ohnmacht | 514/297 |
| 5,272,163 | 12/1993 | Russell et al. | 514/347 |

FOREIGN PATENT DOCUMENTS

| | | |
|---|---|---|
| 0524781 | 1/1993 | European Pat. Off. . |
| WO93/23358 | 11/1993 | WIPO . |

OTHER PUBLICATIONS

P. P. Righetti et al., "Changes in the Reactivity of 2–Oxoindolin–3–Ylidene Derivatives with Ethylvinylether Induced by Electron–Withdrawing Groups. The Importance of the Lumo Coefficients", *Tetrahedron*, (1981), 37, 1779–1785.

Jeffrey J. Morris et al., "Non–Steroidal Antiandrogens. Design of Novel Compounds Based on an Infrared Study of the Dominant Conformation and Hydrogen–Bonding Properties of a Series of Anilide Antiandrogens," *J. Med. Chem.*, (1991), 34, 447–455.

I. Tamm et al., *Structural Requirements of Selective Inhibition of Enteroviruses by 2–(α–Hydroxybenzyl–benzimidazole and Related Compounds*, Nature, 223, 785–88, 1969.

*Primary Examiner*—Matthew V. Grumbling
*Attorney, Agent, or Firm*—Liza D. Hohenschutz

[57] ABSTRACT

Compounds of formula I

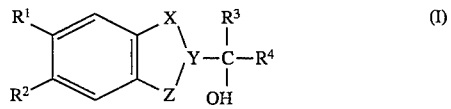

wherein $R^1$–$R^4$, X, Y, and Z have any of the meanings given in the specification, and their pharmaceutically acceptable salts are useful as potassium channel openers for the treatment of urinary incontinence. Also disclosed are pharmaceutical compositions, processes for preparing the compounds of formula I and intermediates.

7 Claims, No Drawings

2-HYDROXYALKYL-BENZIMIDAZOLES, -QUINAZOLINES AND -BENZOTHIAZOLES AS POTASSIUM CHANNEL AGONISTS

This invention relates to a novel group of compounds which are useful in the treatment of bladder instability in mammals such as man. More specifically, this invention relates to this group of compounds, their use in the treatment of urinary incontinence in mammals (including man), processes for preparing them and pharmaceutical compositions containing them.

It is known that bladder tissue is excitable and that urinary incontinence can be caused by uncontrolled or unstable bladder contractions. A group of compounds have been found that are unexpectedly capable of relaxing bladder smooth muscle, thus preventing or ameliorating uncontrolled or unstable bladder contractions. Hence, the compounds may be useful for the treatment of urge incontinence, which includes for example detrusor instability, which may result from cystitis, urethritis, tumors, stones, diverticuli or outflow obstruction; and detrusor hyperreflexia, which may result from stroke, dementia, Parkinsons, suprasacral spinalcord injury or suprasacral spinalcord disease.

This invention provides a compound of formula I (formula set out, together with other formulae referred to by Roman numerals, on pages following the Examples), wherein:

one of $R^1$ and $R^2$ represents hydrogen and the other represents nitro, cyano, halogeno, trifluoromethyl, pentafluoroethyl, trifluoromethoxy, trifluoromethylsulphonyl, methanesulphonyl or a group of formula ArL in which L is CO or $SO_2$; and Ar is pyridyl, pyrimidyl or phenyl, said phenyl being unsubstituted or substituted by one or-two substituents independently selected from halogeno, hydroxy, cyano, (1–4C)alkyl and (1–4C)alkoxy; or $R^1$ and $R^2$ together with the carbon atoms to which they are attached form a 1-oxa-2,5-diazolyl or 1-thia-2,5-diazolyl ring, or an N-oxide thereof;

Y is an $sp^2$-hybridised carbon atom and X, Y and Z, together with the carbon atoms to which they are attached form a 5- or 6-membered heterocyclic ring wherein each ring heteroatom is selected from O, N and S, and one ring carbon atom may optionally be subtituted by hydroxy;

$R^3$ and $R^4$ are independently (1–3C)alkyl substituted by from 0 to 2k+1 atoms selected from fluoro and chloro wherein k is the number of carbon atoms in the said (1–3C)alkyl, provided that $R^3$ and $R^4$ are not both methyl; or $R^3$ and $R^4$ together with the carbon atom to which they are attached, form a 3–5 membered cycloalkyl ring optionally substituted by from 0 to 2m–2 fluorine atoms wherein m is the number of carbon atoms in said ring; or a pharmaceutically acceptable in vivo hydrolyzable ester of said compound of formula I;

or a pharmaceutically acceptable salt of said compound or said ester.

The invention further provides a method for the treatment of urinary incontinence, comprising administering to a mammal (including man) in need of such treatment an effective amount of a compound of formula I as defined above, or a pharmaceutically acceptable in vivo hydrolyzable ester of said compound of formula I or a pharmaceutically acceptable salt of said compound or said ester.

The invention further provides a pharmaceutical composition comprising a compound of formula I as defined above, or a pharmaceutically acceptable in vivo hydrolyzable ester of said compound of formula I or a pharmaceutically acceptable salt of said compound or said ester, and a pharmaceutically acceptable diluent or carrier.

It will be appreciated that certain of the compounds of formula I may exist in tautomeric form and that the invention includes the compounds in each of these forms.

In this specification the terms "alkyl" and "alkoxy" include both straight and branched chain radicals, but it is to be understood that references to individual radicals such as "propyl" or "propoxy" embrace only the straight chain ("normal") radical, branched chain isomers such as "isopropyl" or "isopropoxy" being referred to specifically.

The term "halo" is inclusive of fluoro, chloro, bromo, and iodo unless noted otherwise.

It will be appreciated by those skilled in the art that certain compounds of formula I contain an asymmetrically substituted carbon and/or sulfur atom, and accordingly may exist in, and be isolated in, optically-active and racemic forms. Some compounds may exhibit polymorphism. It is to be understood that the present invention encompasses any racemic, optically-active, polymorphic or stereoisomeric form, or mixtures thereof, which form possesses properties useful in the treatment of urinary incontinence, it being well known in the art how to prepare optically-active forms (for example, by resolution of the racemic form by recrystallization techniques, by synthesis from optically-active starting materials, by chiral synthesis, or by chromatographic separation using a chiral stationary phase) and how to determine efficacy for the treatment of urinary incontinence by the standard tests described hereinafter.

Particular values for a substituent represented by $R^1$ or $R^2$ are nitro, cyano, fluoro, chloro, bromo, iodo, trifluoromethyl, pentafluoroethyl, trifluoromethoxy, trifluoromethylsulphonyl, methanesulphonyl, phenylsulphonyl, benzoyl, 4-pyridylsulphonyl and 4-pyridylcarbonyl. Particularily preferred values include nitro and phenylsulphonyl. Preferably $R^2$ is hydrogen.

Particular values for X—Y—Z are N═C—NH, N═C—S, C(OH)═N—C═N.

Preferably either $R^3$ and $R^4$ both represent difluoromethyl, or $R^4$ represents trifluoromethyl and $R^3$ represents methyl, fluoromethyl, difluoromethyl or trifluoromethyl. More preferably $R^4$ represents trifluoromethyl and $R^3$ represents methyl.

A compound of formula I can be made by processes which include processes known in the chemical arts for the production of structurally analogous compounds. Such processes are provided as further features of the invention and are illustrated by the following procedures in which the meanings of generic radicals are as given above unless otherwise qualified. Such a process can be effected, generally, (a) by reacting a compound of formula II with a carbonyl compound of formula $R^3COR^4$.

The reaction is conveniently performed in the presence of a base such as an alkali metal amide, for example lithium diisopropyl amide. Suitable solvents include ethers such as tetrahydrofuran. Conveniently, the reaction is performed at a temperature in the range of from −110° to 0° C.

(b) for a compound of formula I in which one or $R^1$ and $R^2$ is nitro, by nitrating a compound of formula III.

The nitration is conveniently performed using a nitrating reagent such as a mixture of concentrated nitric acid and concentrated sulfuric acid. Conveniently the nitration is performed at a temperature in the range of from −10° to 75° C.

(c) for a compound of formula I in which X—Y—Z represents N=C—NH, by deprotecting a compound of formula IV in which $R^5$ represents a suitable protecting group.

Examples of suitable protecting groups include silyl ethers such as 2-trimethylsilylethoxymethyl. Silyl ethers may conveniently be removed by treatment with a tetraalkyl ammonium fluoride such as tetrabutylammonium fluoride.

(d) by deprotecting a protected compound of formula V in which $R^6$ represents a suitable alcohol protecting group, such as for example a benzyl group or a silyl protecting group; Examples of suitable reagents for deprotecting a compound of formula II when Pg is benzyl are (1) hydrogen in the presence of palladium-on-carbon catalyst, i.e. hydrogenolysis; or (2) hydrogen bromide or iodide; and when PG is a silyl protecting group are (1) tetrabutylammonium fluoride; or (2) aqueous hydrofluoric acid. The reaction can be conducted in a suitable solvent such as ethanol, methanol, acetonitrile, or dimethylsulfoxide and may conveniently be performed at a temperature in the range of −40° to 100° C.

(e) for a compound of formula I in which X—Y—Z represents C(OH)=N—C=N, reacting a compound of formula VI with formamide.

The reaction is conveniently performed at a temperature in the range of from 100° to 250° C.

(f) for a compound of formula I in which one of $R^1$ and $R^2$ represents ArL and L is CO, reacting the corresponding compound of formula I in which one of $R^1$ and $R^2$ represents iodo with carbon monoxide and the appropriate tetraaryl tin (e.g., tetraphenyltin)in the presence of a carbonylation catalyst.

Suitable carbonylation catalysts include palladium compounds such as palladium(II)dichloride bis(acetonitrile). The reaction is conveniently performed at a temperature in the range of from 0° to 100° C., and at an elevated pressure, preferably in the range of from 10 to 200 psi (170,000 to 3,400,000 pascals). Convenient solvents include ethers such as tetrahydrofuran.

If not commercially available, the necessary starting materials for the procedures such as that described above may be made by procedures which are selected from standard organic chemical techniques, techniques which are analogous to the synthesis of known, structurally similar compounds, or techniques which are analogous to the above described procedure or the procedures described in the examples.

The compounds of formula III in which X—Y—X represents N=C—NH may be prepared by reacting 1,2-phenylenediamine with a compound of formula VII in the presence of a dehydrating agent, for example polyphosphoric acid.

The compounds of formula IV may be prepared from compounds of formula VIII following the method of process (a) described hereinabove.

The compounds of formula VIII may be prepared by reacting the unprotected precursor with an appropriate reagent, for example 2-trimethylsilylethoxymethyl chloride.

In cases where compounds of formula I are sufficiently basic or acidic to form stable acid or basic salts, administration of the compound as a salt may be appropriate, and pharmaceutically acceptable salts may be made by conventional methods such as those described following. Examples of suitable pharmaceutically acceptable salts are organic acid addition salts formed with acids which form a physiologically acceptable anion, for example, tosylate, methanesulfonate, acetate, tartrate, citrate, succinate, benzoate, ascorbate, α-ketoglutarate, and α-glycerophosphate. Suitable inorganic salts may also be formed such as sulfate, nitrate, and hydrochloride.

Pharmaceutically acceptable salts may be obtained using standard procedures well known in the art, for example by reacting a sufficiently basic compound of formula I (or its ester) with a suitable acid affording a physiologically acceptable anion. It is also possible with most compounds of the invention to make a corresponding alkali metal (e.g., sodium, potassium, or lithium) or alkaline earth metal (e.g., calcium) salt by treating a compound of formula I (and in some cases the ester) with one equivalent of an alkali metal or alkaline earth metal hydroxide or alkoxide (e.g. the ethoxide or methoxide in aqueous medium followed by conventional purification techniques.

In vivo hydrolyzable esters of compounds of the invention may be made by coupling with a pharmaceutically acceptable carboxylic acid or an activated derivative thereof. For example, the coupling may be carried out by treating a parent compound of formula I with an appropriate acid chloride (for example, acetyl chloride, propionyl chloride, or benzoyl chloride) or acid anhydride (for example, acetic anhydride, propionic anhydride, or benzoic anhydride) in the presence of a suitable base such as triethylamine. Those skilled in the art will appreciate that other suitable carboxylic acids (including their activated derivatives) for the formation of in vivo hydrolyzable esters are known to the art and these are also intended to be included within the scope of the invention. Catalysts such as 4-dimethylaminopyridine may also be usefully employed.

When used to treat urinary incontinence, a compound of formula I is generally administered as an appropriate pharmaceutical composition which comprises a compound of formula I as defined herein before together with a pharmaceutically acceptable diluent or carrier, the composition being adapted for the particular route of administration chosen. Such compositions are provided as a further feature of the invention.

The compositions may be obtained employing conventional procedures and excipients and binders and may be in a variety of dosage forms. For example, they may be in the form of tablets, capsules, solutions or suspensions for oral administration; in the form of suppositories for rectal administration; in the form of sterile solutions or suspensions for administration by intravenous, intravesicular, subcutaneous or intramuscular injection or infusion; or in the form of a patch for transdermal administration.

Treatment using a compound according to the invention may be remedial or therapeutic as by administering a compound following the onset or development of urinary incontinence in a patient. Treatment may also be prophylactic or prospective by administering a compound in anticipation that urinary incontinence may develop, for example in a patient who has suffered from incontinence in the past.

According to a further aspect, the invention provides the use of a compound of formula I, as defined hereinabove, in the manufacture of a medicament for the treatment of urinary incontinence.

It has also unexpectedly been found that compounds according to the invention are potassium channel openers. It is known that by functioning to open potassium channels, potassium channel opening compounds may thereby function to relax smooth muscle.

Because compounds according to the invention function to open cell potassium channels, they may also be useful as therapeutic agents in the treatment of other conditions or diseases in which the action of a therapeutic agent which opens potassium channels is desired or is known to provide amelioration. Such conditions or diseases include hypertension, asthma, peripheral vascular disease, right heart failure, congestive heart failure, angina, ischemic heart disease, cerebrovascular disease, renal cholic, disorders associated with kidney stones, irritable bowel syndrome, male pattern baldness, premature labor, and peptic ulcers.

The dose of compound of formula I which is administered will necessarily be varied according to principles well known in the art taking account of the route of administration, the severity of the incontinence condition, and the size and age of the patient. In general, a compound of formula I will be administered to a warm blooded animal (such as man) so that an effective dose is received, generally a daily dose of above 0.005, for example in the range of about 0.01 to about 10 mg/kg body weight.

It will be apparent to those skilled in the art that a compound of formula I may be co-administered with other therapeutic or prophylactic agents and/or medicaments that are not medically incompatible therewith. Compounds within the scope of the invention have not been found show any indication of untoward side-effects in laboratory test animals at several multiples of the minimum effective dose.

The actions of compounds of formula I as smooth muscle relaxants useful as therapeutic agents for the treatment of urinary incontinence through their action to open potassium channels and hyperopolarize the membrane electrical potential in bladder detrusor smooth muscle may be shown using suitably designed in vitro tests, such as the one described following. Compounds according to the invention typically exhibit an $IC_{50}$ on the order of 30 micromolar or less in the test. For example, the compound of Example 1 has been found to give an $IC_{50}$ of 8.5 micromolar (um) in the above test. "$IC_{50}$" is a well understood term and means the concentration of test compound which causes a 50% decrease in the in vitro contraction of the bladder tissue described in the following test.

Male albino Hartley guinea pigs (450–500 g) are sacrificed by carbon dioxide induced asphyxiation and quickly exsanguinated. The lower abdominal cavity is opened and the urinary bladder isolated. The bladder is cleaned of surrounding connective and adipose tissue, and the portion above the ureteral orifices is removed and washed in Krebs-Henseleit buffer solution of the following composition (in mM): NaCl 118.0, KCl 4.7, $MgSO_4$ 1.2, $KH_2PO_4$ 1.2, $CaCl_2$ 2.5, $NaHCO_3$ 25.0 and d-glucose 11.1. The solution is warmed to 37° C. and gassed with 95% $O_2$ and 5% $CO_2$. With vigorous bubbling, the solution should have a pH value close to 7.4.

The dome of the washed bladder is cut off and discarded; the remaining bladder is placed on a gauze in a Petri dish containing the buffer solution. A mid-ventral longitudinal cut is made with scissors to open the bladder. The strips cut from the dome and the base edge are discarded. The remaining detrusor mid-section is cut into two horizontal strips with an approximate width of 2.0 mm. These two strips are further bisected at the mid-dorsal section, creating four strip of similar dimensions. Each strip thus contains both dorsal and ventral portions of the bladder.

The two ends of each individual strip are tied to a glass support rod and a force-displacement transducer (Grass model FT03), respectively, with 4-0 black braided silk suture.

The transducers are connected to a polygraph (Grass model 7E), which is calibrated at 5 mV/cm and the calibration checked for linearity with weights of 5 and 0.5 grams.

The analog electrical output signals from the polygraph are digitized by a Modular Instrument Micro 5000 signal processing system using Biowindow Data Acquisition Software, which is run under the Microsoft OS/2 operating system with an IBM-compatible PC.

The detrusor strips on the glass rod are secured in 20 ml tissue baths and allowed to equilibrate under a preload tension of 2 grams. During the following 45 to 60 min equilibration period, the tissue is washed with fresh buffer solution at 15 min interval, with the tension adjusted, if necessary, to 2 grams prior to washing. After the equilibration period, a priming dose of 15 mM KCl (total concentration in the bath) is applied. The tissue is washed after 10 min and washed twice more at 15 min intervals with tension adjusted to 2 grams before each washing.

When the tissue relaxes to a steady state after the final washing, 15 mM KCl is again applied. Once the myogenic activity of the tissue reaches a steady state, the baseline data are acquired through the Biowindows Data Acquisition System by averaging 5 min of the myogenic data sampled at 32 Hz. Once the baseline is acquired, the experimental compounds are dosed in a cumulative manner in half log unit increments. The contact time for each dose is 10 min with the final 5 min being the period of time that the dose response data are acquired. If 30 µM of the test compound does not abolished the detrusor mechanical activity, then 30 µMacromakalim, a putative potassium channel opener, is dosed to establish a maximum response. The effect of the compound at each dose is expressed as % of the maximum inhibitory response, which is further normalized with respect to the corresponding effect of the compound vehicle control. The normalized response is then used to derive the $IC_{50}$ of the relaxant activity of the compound through the application of Marquardt's nonlinear iterative curve fitting technique to a standard dose-response function.

The ability of compounds according to the invention to open potassium channels in detrusor smooth muscle can be further demonstrated by a second in vitro test. This second in vitro test is similar to the one described above with regard to tissue preparation and data acquisition. However, the following exceptions are noted. In this second test, the contraction of the detrusor strips during priming and after the equilibration period is achieved with 80 mM instead of 15 mM KCl (total concentration in the bath). A sustained tension in the tissue is evident after this high KCl stimulation, because voltage-sensitive calcium channels have been rendered open to permit an influx of calcium into the cells and the development of tonic tension. This tension is totally abolished with 300 µM of paparefine, which is thereby used to establish the maximum response in this test.

Typical calcium channel blockers like nifedipine, nimodipine, isradipine, and verapamil are able to relax and reduce the myogenic activity of guinea pig detrusor strips in both tests by virtue of their blocking action on calcium channels. However, all of the aforementioned calcium channel blockers are more potent in the second test when 80 mM KCl is used, than in the first test where 15 mM KCl is used. In contrast, while the putative potassium channel opener cromakalim has a potent relaxant activity in the first test with an $IC_{50}$ in the range of 0.6 to 0.9 µM, it demonstrates insignificant relaxant activity in the second test at concentrations as high as 30 µM. Thus, the profile of a higher relaxant activity in the first test than in the second of compounds according to the invention indicates that the compounds are functioning as potassium channel openers.

The ability of the compounds according to the invention to act as potassium channel openers on bladder tissue may be further demonstrated by a standard test which measures the effect of test compounds on the rate of efflux of rubidium ($^{86}$Rb) or potassium ($^{42}$K) from the tissue.

The following is a description of a test in vivo which is complimentary to the above described test and which may be used to ascertain if a test compound is active and, additionally, if the test compound exhibits selectivity for the bladder without significant cardiovascular effects when dosed orally.

Male Wistar rats (400–500 g) were anesthetized with 50 mg/kg Nembutal, i.p. For each rat, the abdominal region and the front and back of the neck were shaved and povidone-iodine was applied to the skin. For carotid catheterization, the left carotid artery was exposed via a small ventral cervical incision. The exposed area was flushed with a 2% lidocaine HCl solution to relax the vessel. The catheter, filled with 0.9% saline, was introduced approximately 2.4 cm into the artery so that its tip resided in the aortic arch. The distal end of the catheter was exteriorized at the nape of the neck, filled with heparin (1000 units/ml) and heat sealed. For bladder catheterization, the bladder was exposed through a midline abdominal incision. A trocar was passed through the abdominal muscle about 1 cm from the upper end of the incision and then tunneled subcutaneously to emerge through the skin at the back of the neck. A saline-filled catheter was passed through the trocar. A small opening in the bladder dome was created with an Accu-Temp cautery. The catheter was placed into the bladder and secured with a 4-0 silk ligature. The catheter was flushed with saline and patency was noted. The external end of the catheter was heat-sealed to prevent urine leakage. The abdominal muscles and the skin were sutured. Both catheters were threaded through a stainless steel anchor button (Instech), which was then sutured to the subcutaneous muscle at the point of exteriorization. The skin was sutured closed over the button. The animals were allowed to recover from anesthesia.

24–48 hours after surgery, each rat was placed in a metabolism cage and connected via the anchor button to an Instech spring tether and swivel system to protect the catheters from damage and to allow the animal free movement in the cage. The carotid catheter was connected to a Gould P23XL pressure transducer for blood pressure measurement. The bladder catheter was connected to a pump for saline infusion and to a pressure transducer by means of PE50 tubing and a 4-way stopcock. A toploading balance with a collection cup was placed under the cage for urine output measurement.

The rats were weighed, orally sham-dosed (dosing needle introduced, but no fluid expelled), and transvesical saline infusion (0.18 ml/min) was begun and continued throughout the experiment. Variations in blood pressure, heart rate, intravesical pressure and urine output were recorded on either a Grass Polygraph or a Gould TA4000 recording system. The animals were allowed to equilibrate until the micturition pattern became consistent (approx. 45–90 min.). At this point, a basal level of each experimental parameter was recorded and the rats were administered by oral gavage the appropriate dose of compound (in a 75% PEG 400—saline vehicle) in concentrations such that the volume was 1 ml/kg body weight. The effects of the compounds on experimental parameters were followed for five hours after administration.

Experimental results for both the interval between contractions and also heart rates were expressed as the mean ±S.E.M. (Standard Error of Measures) % change from basal level, with each animal serving as its own control. MAP is expressed as mean ±S.E.M mm Hg change from basal level.

Compounds according to the invention are active in one or more of the above-described tests.

The invention will now be illustrated by the following non-limiting examples in which, unless stated otherwise:

(i) temperatures are given in degrees Celsius (°C.); operations were carried out at room or ambient temperature, that is, at a temperature in the range of 18°–25° C.;

(ii) organic solutions were dried over anhydrous magnesium sulfate; evaporation of solvent was carried out using a rotary evaporator under reduced pressure (600–4000 pascals; 4.5–30 mm Hg) with a bath temperature of up to 60° C.;

(iii) chromatography means flash chromatography on silica gel; thin layer chromatography (TLC) was carried out on silica gel plates;

(iv) in general, the course of reactions was followed by TLC and reaction times are given for illustration only;

(v) melting points are uncorrected and (dec) indicates decomposition; the melting points given are those obtained for the materials prepared as described; polymorphism may result in isolation of materials with different melting points in some preparations;

(vi) final products had satisfactory proton nuclear magnetic resonance (NMR) spectra;

(vii) yields are given for illustration only and are not necessarily those which can be obtained by diligent process development; preparations were repeated if more material was required;

(viii) when given, NMR data is in the form of delta values for major diagnostic protons, given in parts per million (ppm) relative to tetramethylsilane (TMS) as an internal standard, determined at 300 MHz using perdeuterio dimethyl sulfoxide (DMSO-$d_6$) as solvent; coupling constants (J) are given in Hz; Ar designates an aromatic proton when such an assignment is made;

(ix) chemical symbols have their usual meanings; SI units and symbols are used;

(x) reduced pressures are given as absolute pressures in pascals (Pa); elevated pressures are given as gauge pressures in bars;

(xi) solvent ratios are given in volume:volume (v/v) terms; and (xii) mass spectra (MS) were run with an electron energy of 70 electron volts in the chemical ionization (CI) mode using a direct exposure probe; where indicated ionization was effected by electron impact (EI) or fast atom bombardment (FAB); values for m/z are given; generally, only ions which indicate the parent mass are reported.

EXAMPLE 1

1,1,1-Trifluoro-2-(5-nitrobenzimidazol-2-yl)propan-2-ol

To stirred concentrated sulfuric acid (11 mL) was added 1,1,1-trifluoro-2-benzimidazol-2-ylpropan-2-ol (3.00 g) under a nitrogen atmosphere while maintaining the temperature at 5° C. The reaction mixture was treated with a nitrating reagent (3.5 mL) containing concentrated nitric acid and concentrated sulfuric acid (1.5 mL), while maintaining the reaction temperature below 35° C., and was then stirred for 1 hour at ice bath temperature. The reaction mixture was then poured onto ice, neutralized to pH 7–8, extracted with diethyl ether, and dried. The solvent was evaporated to leave a gold oil. Trituration of the oil with diethyl ether provided the title compound as a white solid (0.80 g); mp 73°–75° C., resolidified mp 173°–174° C.; NMR (250 MHz): 1.68 (s,3), 7.62 (s,1), 7.78 (broad d,1), 8.19 (dd,1), 8.52 (s,1), 13.4 (s,1); MS: m/z=276(M+1). Analysis for $C_{10}H_8F_3N_3O$: Calculated C, 43.65; H, 2.93; N, 15.27; Found: C, 43.32; H, 3.02; N, 15.03.

The starting material was prepared as follows.

a. 1,1,1-Trifluoro-2-benzimidazol-2-ylpropan-2-ol. A mixture of 1,2-phenylenediamine (684 mg), 3,3,3-trifluoro-2-hydroxy-2-methylpropanoic acid (1.00 g), and polyphosphoric acid (large excess), were heated at 150° C. for 48 hours under a nitrogen atmosphere. The reaction mixture was then poured onto ice, neutralized to pH 7, and extracted with diethyl ether. The ether layer was washed (brine), dried, and evaporated to leave a brown solid. Chromatography, eluting with methanol:chloroform (gradient 0–5% MeOH in $CHCL_3$), provided 1,1,1-trifluoro-2-benzimidazol-2-ylpropan-2-ol as a tan solid (110 mg); mp 184°–187° C.; NMR (250 Hz): 1.81 (s,3), 7.19 (m,2), 7.28 (s,1), 7.47 (d,1), 7.62 (d,1), 12.80 (s,1); MS: m/z=231(M+1). Analysis $C_{10}H_9F_3N_2O$: Calculated: C, 52.19; H, 3.94; N, 12.17; Found: C, 52.47; H, 4.11; N, 11.71.

EXAMPLE 2

1,1,1-Trifluoro-2-(5-nitrobenzothiazol-2-yl)propan-2-ol

A solution of 5-nitrobenzothiazole (120 mg) in dry tetrahydrofuran (10 mL was cooled to −100° C. and then treated dropwise with lithium diisopropylamide (0.36 mL, 2.0M). The reaction mixture was stirred for 40 minutes at −100° C., and then treated with a solution of trifluoroacetone (75 mg) in dry tetrahydrofuran (1 mL). The reaction mixture was maintained at −100° C. for 30 minutes, treated with saturated aqueous ammonium chloride (10 mL), warmed to room temperature, and extracted with diethyl ether. The extracts were combined, washed (brine) dried ($Na_2SO_4$), and evaporated to leave a brown solid. Chromatography, eluting with chloroform, followed by chromatography, eluting with toluene, gave the title compound as a solid (100 mg); m.p. 66°–69° C.; NMR: 1.87 (s,3), 8.10 (s,1), 8.33 (dd,1), 8.46 (d,1), 8.87 (d,1); MS (EI, high resolution): 292.0144 (theoretical 292.01292). Analysis for $C_{10}H_7F_3N_2O_3S$: Calculated: 41.10; H, 2.41; N, 9,59; Found: C, 39.32; H, 3.09; N, 8,26.

EXAMPLE 3

1,1,1-Trifluoro-2-(5-phenylsulfonylbenzothiazol-2-yl)-propan-2-ol

To a stirred solution of 5-phenylsulfonylbenzothiazole (0.845 g) in dry tetrahydrofuran (50 mL) at −78° C. was added lithium diisopropylamide (3.5 mmol in 3 mL tetrahydrofuran) dropwise over approximately 10 minutes. A deep red solution formed. Trifluoroacetone (0.63 g) was added. After stirring for 20 minutes at −78° C., the reaction mixture was quenched with saturated ammonium chloride solution. The reaction mixture was then extracted with ether (75 mL and 25 mL) and dichloromethane (25 mL). The combined organic layers were dried, filtered and purified by chromatography, eluting with ethyl acetate:hexane (gradient of 10 to 30% ethyl acetate), to give the title compound as a white solid (0.558 g); m.p. 126.5°–128.5° C.; NMR: 8.62 (d,1), 8.43 (d,1), 8.01–8.07 (m,4), 7.60–7.70 (m,3), 1.84 (s,3); MS: m/z=388(M+1). Analysis for $C_{16}H_{12}F_3NO_3S_2$: Calculated: C,49.61; H,3.12; N, 3.62: Found: C, 49.43; H, 3.23; N, 3.56.

The starting material was prepared as follows:

a. 5-Phenylsulfonylbenzthiazole. 6-Nitro-4-phenylsulfonylchlorobenzene (2.91 g) and sodium sulfide nonahydrate (6.37 g) were suspended in water (50 mL) and heated to reflux. The mixture was stirred at reflux for 4.5 hours, cooled, and acidified to pH 2.0 with dilute hydrochloric acid. After standing for 16 hours, the solution was evaporated to dryness and triturated with toluene to give a brown solid. The crude product was then added to formic acid (40 mL) and the mixture heated under reflux for 2 days. After evaporation, the resulting solid was partitioned between dichloromethane (75 mL) and water, (75 mL). The aqueous layer was further extracted with dichloromethane (2×50 mL). The combined organic layers were washed (water) dried, decolorized (charcoal) and evaporated to give the crude product. Chromatography, eluting with ethyl acetate:hexanes (gradient 10–25% ethyl acetate in hexanes) gave 5-phenylsulfonylbenzthiazole (0.845 g); NMR: 9.6 (s,1), 8.64 (d,1), 8.45 (d,1), 8.00–8.07 (m,3), 7.60–7.72 (m,3); MS: m/z=276(M+1).

EXAMPLE 4

1,1,1-Trifluoro-2-(5-phenylsulfonylbenzimidazol-2-yl)-propan-2-ol

To a stirred solution of a mixture of regio isomers of 1,1,1-trifluoro-2-[1-(2-trimethylsilylethoxymethyl)-5-phenylfonylbenzimidazol- 2-yl]propan-2-ol (2.19 g), prepared as described in sub-part c. below, in dry tetrahydrofuran (30 mL) was added tetrabutylammonium fluoride (7.9 mL of 1M solution in tetrahydrofuran). After stirring overnight at reflux, additional tetrabutylammonium fluoride (1.2 mL) was added. The solution was heated to reflux where it was maintained for 4.5 hours. The reaction was then quenched with pH 7.0 phosphate buffer and extracted with diethyl ether (2×100 mL) and dichloromethane (2×75 mL). The combined organic layers were dried, evaporated and purified by chromatography, eluting with ethyl acetate:hexanes with (gradient of 25% to 50% ethyl acetate in hexanes) to give the title compound as a white solid (0.885 g); m.p. 115°–117° C.; NMR: 8.28 (broad and s,1), 7.49–8.07 (m,7), 1.81 (s,3); MS: m/z=371(M+1). Analysis for $C_{16}H_{13}F_3N_2O_3S$. 0.25 $H_2O$: Calculated: C, 51.28; H, 3.63; N, 7.47; Found: C, 51.03; H, 3.49; N, 7.17.

The starting material was prepared as follows.

a. 5-Phenylsulfonylbenzimidazole. 2-Nitro-4-phenylsulfonylaniline (8.7 g) was dissolved in formic acid (50 mL). Palladium on carbon (0.62 g of 10%) was added to the solution. The reaction mixture was hydrogenated (3.5 bar) for 5 hours. After filtering through diatomaceous earth the reaction mixture was refluxed for 2 days. The cooled solution was evaporated to low volume and triturated with toluene, affording an orange-brown solid which was dried in vacuo to give 5-phenylsulfonylbenzimidazole (5.39 NMR: 8.48 (s,1), 8.24 (broad s,1), 7.97 (broad d,2), 7.76 (broad s,2), 7.56–7.66(m, 4); MS: m/z=259(M+1).

b. 1-(2-Trimethylsilylethyloxymethyl)-5-phenylsulfonylbenzimidazole and 1-(2-trimethylsilylethyloxymethyl)-6-phenylsulfonylbenzimidazole (1:1 mixture). The product of step a. (3.06 g), in tetrahydrofuran (25 mL) was added dropwise to a stirred suspension of sodium hydride (0.625 g of 50% in oil) in dry dimethylformamide (15 mL) at 0° C. over ten minutes. After hydrogen evolution had ceased 2-trimethylsilylethoxymethyl chloride (2.41 g) in dimethylformamide (10 mL) was added dropwise. The reaction mixture was allowed to warm to room temperature where it was stirred for 16 hours. The reaction mixture was poured into water (100 mL). The aqueous mixture was extracted with dichloromethane (4×50 mL). The combined organic layers were washed (water) dried, evaporated, and purified by chromatography, with ethyl acetate:hexane (gradient of 20–55% ethyl acetate) as the eluent, to give the product, contaminated with dimethylformamide. The product was dissolved in dichloromethane and washed (water). The organic layer was dried and evaporated to give the N-protected compound as a mixture of regioisomers (3.02 g); NMR: 8.66 and 8.63 (s,1), 8.37 and 8.30 (broad s,1, ArH for both isomers), 7.57–8.01 (m, 7, ArH for both isomers), 5.77 and 5.68 (s,2, NCH$_2$O for both isomers), 3.47 (overlapping t,2, OCH$_2$ for both isomers), 0.80 (overlapping t,2, CH$_2$Si for both isomers), −0.12 and −0.14 (s,9, Si(CH$_3$)$_3$ for both isomers); MS: m/z=389(M+1).

c. 1,1,1-Trifluoro-2-[1-(2-trimethylsilylethoxymethyl)-5-phenylsulfonylbenzimidazol-2-yl]propan-2-ol and 1,1,1-Trifluoro-2-[1-(2-trimethylsilylethoxymethyl)-6-phenylsulfonylbenzimidazol-2-yl] -propan-2-ol. To a solution of the product of step b., (3.02 g) in dry tetrahydrofuran (30 mL) at −78° C. was added LDA (8.94 mmol in 6 mL tetrahydrofuran) over 5 minutes. After stirring for 25 minutes trifluoroacetone (1.31 g) was added. The solution was stirred at −78° C. for a further 30 minutes before being quenched with saturated ammonium chloride solution. The reaction mixture was then extracted with ether (3×75 mL) and dichloromethane (2×50 mL). The combined organics were dried, filtered, and evaporated. Chromatography, eluting with ethyl acetate:hexanes (gradient 15%–35% ethyl acetate), gave the alcohol (2.19 g) as a mixture of regioisomers; NMR: 8.37 (broad s,1, ArH, isomer 1), 8.35 (s,1, ArH, isomer 2), 7.57–8.03 (m, ArH and OH for both isomers), 5.87–6.16 (overlapping AB quartets for isomer 1 and 2,2, NCH$_2$O), 3.54–3.61 (m,2, OCH$_2$), 1.92 (s,3, CH$_3$), 0.82 (t,3, J=8.1 Hz, CH$_2$Si), −0.09(s,9, Si(CH$_3$)$_3$); MS: m/z=501(M+1).

EXAMPLE 5

1,1,1-Trifluoro-2-(6-iodoquinazolin-4-one-2-yl)-propan-2 -ol

A solution of N-(2-carboxy-4-iodophenyl)-3,3,3 -trifluoro-2-hydroxy-2-methylpropanamide (5 g) and formamide (5 mL) was stirred and heated at 190°–200° C. for 3 hours. The cooled reaction mixture was poured into brine (150 mL) and extracted with ethyl acetate. The ethyl acetate solution was dried (Na$_2$SO$_4$) and evaporated. Chromatography, eluting with ethyl acetate, gave the title compound (2.86 g) as a white solid; mp 205°–207° C.; NMR: 1.75 (s,3), 7.48 (d,1), 7.5 (s,1), 8.13 (d,1), 8.42 (s,1), 12.05 (s,1); MS: m/z=385(M+1). Analysis for C$_{11}$H$_8$F$_3$IN$_2$O$_2$: Calculated: C, 34.40; H, 2.10; N, 7.29; Found: C, 34.48; H, 2.09; N, 7.26.

The starting material was prepared as follows.

a. N-(2-Carboxy-4-iodophenyl)-3,3,3-trifluoro-2-hydroxy-2-methylpropanamide. Thionyl chloride (5 g) was slowly added to a stirred solution of 2-hydroxy-2-trifluoromethyl propionic acid (6.64 g) in dimethylacetamide (100 mL) cooled to and maintained at −15° C. After 1 hour, 5-iodoanthranilic acid (10 g) was added in one portion and the temperature was allowed to slowly rise to ambient temperature. After stirring overnight, the reaction mixture was poured into water (1500 mL). The aqueous mixture was treated with solid sodium bicarbonate to pH 4, filtered, washed (water), and dried to give the amide (13.1 g) as a tan solid; mp 240°–243° C. Leaching with cold methylene chloride raises the mp to 247°–250° C.; NMR: 1.58 (s,3), 7.74 (s,1), 7.96 (d,1), 8.28 (s,1), 8.45 (d,1), 12.28 (s,1); MS: m/z=404(M+1).

EXAMPLE 6

1,1,1-Trifluoro-2-(6-phenylsulfonylquinazolin-4-one-2-yl)-propan-2-ol

2-Acetoxy-N-(2-carboxy-4-phenylsulfonylphenyl)-3,3,3 -trifluoro-2-methylpropionamide (100 mg) and formamide (2 mL) were mixed and heated at reflux for 1 hour. The reaction mixture was then cooled, poured into water and extracted with ethyl acetate. The ethyl acetate was washed (water, brine) dried (Na$_2$SO$_4$) and evaporated. The crude solid was treated with charcoal in ethyl acetate, and then crystallized from warm ethyl acetate by addition of hexanes to the cloud point, to give the title compound (69 mg) as white needles; mp 202°–204° C.; NMR: 1.73 (s,3), 7.62–7.73 (m,4), 7.86 (d,1), 8.01 (d,2), 8.27 (d,1), 8.59 (s,1); MS: m/z=399(M+1). Analysis for C$_{17}$H$_{13}$F$_3$N$_2$O$_4$S.0.1 C$_4$H$_8$O$_2$: Calculated: C, 51.33; H, 3.42; N, 6.88; Found: C, 51.70; H, 3.58; N, 6.98.

The starting material was prepared as follows.

a. 2-Nitro-5-phenylsulfonylbenzoic acid. To a solution of 2-nitro-5-phenylthiobenzoic acid (13.2 g) in glacial acetic acid (370 mL) was added a solution of potassium permanganate (8.41 g) in water (110 mL) with vigourous stirring. The reaction mixture was stirred overnight. Sodium bisulfite (7.5 g) was added and the clear, yellow solution was poured into water. Acidification to pH 1 with 6N hydrochloric acid gave a solid that was filtered, washed (water) and dried to give the sulfonyl compound as a fine, white solid (11.3 g); mp 228°–230° C.; NMR: 7.76–7.80 (m,3), 8.09 (d,2), 8.22 (d,1), 8.37–8.40 (m,2); MS: m/z=308(M+1).

2-Nitro-5-phenylthiobenzoic acid was prepared as described in J. O. Jilek et al, *Collection Czechoslov. Chem. Commun.* 1979, 44, 2124.

b. 2-Amino-5-phenylsulfonylbenzoic acid. The sulfonyl product from sub-part a. above (11.2 g), in ethanol (150 mL) was hydrogenated in the presence of 10% Pd/C. The catalyst was filtered (diatomaceous earth), the filter pad washed with hot ethanol and the combined filtrate/washings were concentrated to give the amine (7.76 g) as a straw-coloured solid; mp 238°–240° C.; NMR: 6.88 (d,1), 7.56–7.73 (m,4), 7.88 (d,2), 8.23 (s,1); MS: m/z=278(M+1).

c. 2-Acetoxy-N-(2-carboxy-4-phenylsulfonylphenyl)-3,3,3 -trifluoro-2-methylpropionamide. 2-Acetoxy-3,3,3-trifluoro-2-methylpropionyl chloride (1 g), was added to a cold solution of the product of step b. (1.28 g), triethylamine (0.48 g), and dimethylacetamide. The reaction mixture was stirred overnight at room temperature, poured into water, and acidified to pH 2 with 6N hydrochloric acid to give a yellow solid. The solid was filtered, washed (water) and dried. The crude solid was extracted with hot ethyl acetate (100 mL) and filtered. The filtrate was evaporated. The recovered solid was stirred with ether and filtered to give 2 -acetoxy-N-(2-carboxy-4-phenylsulfonylphenyl)-3,3,3-trifluoro-2-methylpropionamide.

The intermediate 2-acetoxy-3,3,3-trifluoro-2-methylpropionyl chloride was prepared as follows.

d. 2-Acetoxy-3,3,3-trifluoro-2-methylpropionyl chloride. Acetyl chloride (6.4 g) was added dropwise to 3,3,3-trifluoro-2 -hydroxy-2-methylpropionic acid (5 g) with ice cooling. The ice bath was removed and the mixture stirred overnight. The mixture was allowed to reflux for 2 hours. Excess acetyl chloride was distilled and the recovered oil was treated with thionyl chloride (ice cooling), followed by reflux for 2 hours. The acetoxy compound was distilled (62°–63° C., 38 mm) and collected as a clear, colourless oil (3.69 g); NMR: 1.72 (s,3), 2.13 (s,3).

EXAMPLE 7

1,1,1-Trifluoro-2-(6-phenylcarbonylquinazolin-4-one-2-yl)propan-2-ol 1,1,1-Trifluoro-2-(6-iodoquinazolin-4-one-2-yl)propan-2-ol (0.5 g), tetraphenyltin (0.833 g) and palladium (II) dichloride bis(acetonitrile) (13.5 mg) were added to a mixture of tetrahydrofuran (10 mL) and 1,3-dimethyl-3,4,5,6-tetrahydro-2(1H)pyrimidinone (5 mL). The reaction mixture was heated to 65° C. in a bomb pressurized with carbon monoxide (approximately 6.9 bar) for 16 hours. The green solution was diluted with ethyl acetate and washed (water) three times. The organic layer was dried and evaporated. Chromatography, eluting with ethyl acetate:hexane (gradient 20–30% ethyl acetate in hexane), and trituration with ether gave the title compound as a white solid (70 mg); mp 161°–163° C.; NMR: 12.1 (s,1), 8.40 (s,1), 8.19 (dd,1), 7.54–7.86 (m,7), 1.78 (s,3); MS: m/z=363(M+1). Analysis for $C_{18}H_{13}N_2O_3F_3$: Calculated: C, 58.67; H, 3.62; N, 7.73; Found: C, 58.54; H, 3.74; N, 7.69.

EXAMPLE 8

The following illustrate representative pharmaceutical dosage forms containing a compound of formula I, for example as illustrated in any of the previous Examples, (hereafter referred to as "compound X"), for therapeutic or prophylactic use in humans:

|  | mg/tablet |
|---|---|
| (a)Tablet |  |
| Compound X | 50.0 |
| Mannitol, USP | 223.75 |
| Croscarmellose sodium | 6.0 |
| Maize starch | 15.0 |
| Hydroxypropylmethylcellulose (HPMC), USP | 2.25 |
| Magnesium stearate | 3.0 |
| (b)Capsule |  |
| Compound X | 10.0 |
| Mannitol, USP | 488.5 |
| Croscarmellose sodium | 15.0 |
| Magnesium stearate | 1.5 |

The above formulations may be obtained by conventional procedures well known in the pharmaceutical art. The tablets may be enteric coated by conventional means, for example to provide a coating of cellulose acetate phthalate.

CHEMICAL FORMULAE

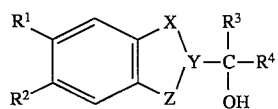

I

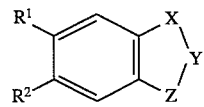

II

-continued
CHEMICAL FORMULAE

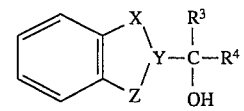

III

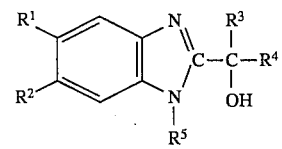

IV

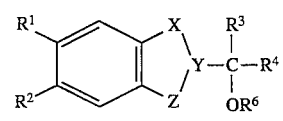

V

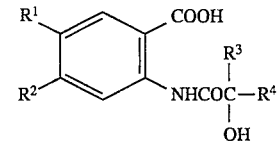

VI

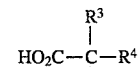

VII

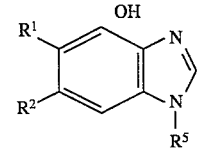

VIII

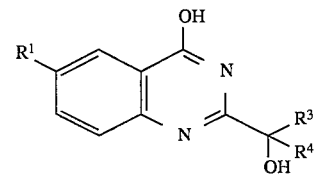

IX

What is claimed is:

1. A compound of formula I:

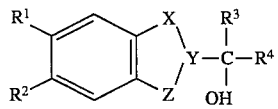

(I)

wherein, one of $R^1$ and $R^2$ represents hydrogen and the other represents nitro, cyano, halogeno, trifluoromethyl, pentafluoroethyl, trifluoromethoxy, trifluoromethylsulphonyl, methanesulphonyl or a group of formula ArL in which L is CO or $SO_2$; and Ar is pyridyl, pyrimidyl or phenyl, said phenyl being unsubstituted or substituted by one or two substituents independently selected from halogeno, hydroxy, cyano, (1–4C)alkyl and (1–4C)alkoxy; or $R^1$ and $R^2$ together with the carbon atoms to which they are attached form a 1-oxa-2,5-diazolyl or 1-thia-2,5-diazolyl ring, or an N-oxide thereof;

X—Y—Z is selected from N=C—NH, N=C—S and C(OH)=N—C=N;

$R^3$ and $R^4$ are independently (1–3C)alkyl substituted by from 0 to 2k+1 atoms selected from fluoro and chloro wherein k is the number of carbon atoms in the said (1–3C)alkyl, provided that $R^3$ and $R^4$ are not both methyl; or $R^3$ and $R^4$, together with the carbon atom to which they are attached, form a 3–5 membered cycloalkyl ring optionally substituted by from 0 to 2m–2 fluorine atoms wherein m is the number of carbon atoms in said ring; or a pharmaceutically acceptable in vivo hydrolyzable ester of said compound of formula I; or a pharmaceutically acceptable salt of said compound or said ester.

2. A compound as claimed in claim 1, wherein $R^1$ is selected from nitro, cyano, fluoro, chloro, bromo, iodo, trifluoromethyl, pentafluoroethyl, trifluoromethoxy, trifluoromethylsulphonyl, methanesulphonyl, phenylsulphonyl, benzoyl, 4-pyridylsulphonyl and 4-pyridylcarbonyl; $R^2$ is hydrogen; and $R^3$ and $R^4$ are both difluoromethyl, or $R^4$ is trifluoromethyl and $R^3$ is methyl, fluoromethyl, difluoromethyl or trifluoromethyl.

3. A compound as claimed in claim 2, wherein $R^4$ is trifluoromethyl and $R^3$ is methyl.

4. A compound as claimed in claim 1, wherein said compound of formula I is a compound of formula IX:

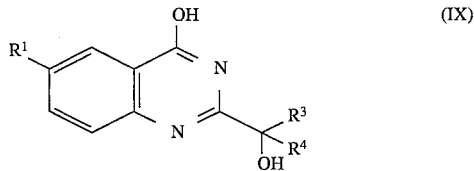

wherein $R^1$, $R^3$, and $R^4$ have the meanings defined in claim 1.

5. A compound as claimed in claim 1, which is selected from:
1,1,1-Trifluoro-2-(5-nitrobenzimidazol-2-yl)propan-2-ol;
1,1,1-Trifluoro-2-(5-nitrobenzothiazol-2-yl)propan-2-ol;
1,1,1-Trifluoro-2-(5-phenylsulfonylbenzothiazol-2-yl)propan-2-ol;
1,1,1-Trifluoro-2-(5-phenylsulfonylbenzimidazol-2-yl)propan-2-ol;
1,1,1-Trifluoro-2-(6-iodoquinazolin-4-one-2-yl)propan-2-ol;
1,1,1-Trifluoro-2-(6-phenylsulfonylquinazolin-4-one-2-yl)propan-2-ol;
and 1,1,1-Trifluoro-2-(6-phenylcarbonylquinazolin-4-one-2-yl)-propan- 2-ol; and pharmaceutically acceptable salts thereof.

6. A compound as claimed in claim 1, which is selected from 1,1,1-Trifluoro-2-(6-phenylsulfonylquinazolin-4-one-2-yl)propan-2-ol; and 1,1,1-Trifluoro-2-(6-phenylcarbonylquinazolin-4-one-2-yl)-propan- 2-ol; and pharmaceutically acceptable salts thereof.

7. A pharmaceutical composition comprising a compound of formula I:

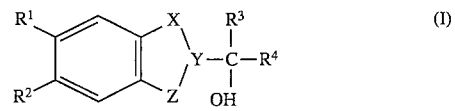

wherein, one of $R^1$ and $R^2$ represents hydrogen and the other represents nitro, cyano, halogeno, trifluoromethyl, pentafluoroethyl, trifluoromethoxy, trifluoromethylsulphonyl, methanesulphonyl or a group of formula ArL in which L is CO or $SO_2$; and Ar is pyridyl, pyrimidyl or phenyl, said phenyl being unsubstituted or substituted by one or two substituents independently selected from halogeno, hydroxy, cyano, (1–4C)alkyl and (1–4C)alkoxy; or $R^1$ and $R^2$ together with the carbon atoms to which they are attached form a 1-oxa-2,5-diazolyl or 1-thia-2,5-diazolyl ring, or an N-oxide thereof;

X—Y—Z is selected from N=C—NH, N=C—S and C(OH)=N—C=N;

$R^3$ and $R^4$ are independently (1–3C)alkyl substituted by from 0 to 2k+1 atoms selected from fluoro and chloro wherein k is the number of carbon atoms in the said (1–3C)alkyl, provided that $R^3$ and $R^4$ are not both methyl; or $R^3$ and $R^4$, together with the carbon atom to which they are attached, form a 3–5 membered cycloalkyl ring optionally substituted by from 0 to 2m–2 fluorine atoms wherein m is the number of carbon atoms in said ring;

or a pharmaceutically acceptable in vivo hydrolyzable ester of said compound of formula I; or a pharmaceutically acceptable salt of said compound or said ester; and a pharmaceutically acceptable diluent or carrier.

* * * * *